United States Patent [19]

Feldman

[11] 4,136,111

[45] Jan. 23, 1979

[54] PROCESS FOR THE PRODUCTION OF PYRUVIC ACID

[75] Inventor: Charles F. Feldman, Fresno, Calif.

[73] Assignee: Hill Brothers Chemical Company, Inc., Orange, Calif.

[21] Appl. No.: 738,070

[22] Filed: Nov. 2, 1976

[51] Int. Cl.² .................. C07C 51/38; C07C 59/34
[52] U.S. Cl. .................................................. 562/577
[58] Field of Search .................... 260/531 R, 526 R

[56] References Cited

U.S. PATENT DOCUMENTS 3,153,083  10/1964  Smidt et al. .................. 260/526 R
3,524,880  8/1970  Lee et al. .................... 260/526R Primary Examiner—Vivian Garner
Attorney, Agent, or Firm—Lyon & Lyon

[57] ABSTRACT

An improved process for forming pyruvic acid comprising reacting a salt of bitartrate, e.g. potassium bitartrate, with concentrated sulfuric acid at an elevated temperature to produce pyruvic acid. The process preferably utilizes approximately equal molar quantities of the potassium bitartrate and sulfuric acid and the reaction is preferably carried out at a temperature of approximately 160° C to approximately 270° C for a period of approximately one half hour to one hour.

8 Claims, No Drawings

PROCESS FOR THE PRODUCTION OF PYRUVIC ACID

BACKGROUND OF THE INVENTION

The present invention relates to pyruvic acid and, in particular, to an improved method for the production of pyruvic acid.

Pyruvic acid is used as a flavor enhancer and as an intermediate compound in biochemical reactions. Heretofore, pyruvic acid has been generally prepared in commercial quantities by the thermal decomposition of tartaric acid in the presence of a suitable dehydration agent.

The tartaric acid was obtained from the reaction of sulfuric acid with an aqueous solution of potassium bitartrate, which is a natural product. The most widely used dehydration agents were potassium bisulfate and potassium pyrosulfate. The reaction was as follows:

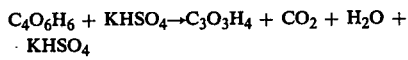

Unfortunately, the yield of pyruvic acid product from the reaction is relatively low, i.e., approximately 60%, which results in a relatively expensive pyruvic acid product. The unfavorable economic effect of the low yield is compounded by the fact that tartaric acid itself is a relatively expensive starting material. Therefore, the art has long sought a straightforward and inexpensive method for producing pyruvic acid. This search has resulted in the development of other methods for the production of pyruvic acid. For example, it was found that pyruvic acid can be prepared by the hydrolysis of acetyl cyanide or oxalacetic ester or by the distillation of glyceric acid in the presence of a dehydrating agent. However, these methods have proved to be of only academic interest and are not adaptable to commercial use due to the high cost of the starting materials and the low reaction yields.

SUMMARY OF THE INVENTION

The process of the invention fills the long felt need for a high yield straightforward method of producing an inexpensive pyruvic acid and comprises reacting in a single step potassium bitartrate (cream of tartar) with concentrated sulfuric acid at an elevated temperature to produce pyruvic acid. The process preferably utilizes approximately equal molar quantities of the potassium bitartrate and sulfuric acid and the reaction is preferably carried out at a temperature of approximately 160° C. to approximately 270° C. for a period of approximately one half hour to one hour. The pyruvic acid is preferably recovered by distillation from the reaction mixture.

Although the reaction chemistry appears simple, in practice the reaction produces an excessive amount of foam which, if uncontrolled, would render the process unworkable. Therefore, careful steps, such as those described below, must be taken to control the foam whereby the reaction may proceed to completion and the pyruvic acid may be readily recovered.

A more thorough disclosure of the advantages of the present invention and the means for obtaining them is presented in the detailed description which follows.

DETAILED DESCRIPTION OF THE INVENTION

The present invention relates to an improved process for the production of pyruvic acid comprising reacting potassium bitartrate with concentrated sulfuric acid at an elevated temperature to form pyruvic acid according to the following reaction:

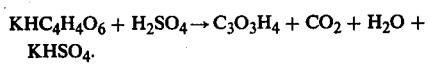

In an alternative embodiment, other salts of bitartrate, such as the sodium salt, may be substituted for the potassium bitartrate in this reaction. Preferably, commercial bitartrate (98% pure) is utilized in the practice of the present invention.

One hundred mole percent of the potassium bitartrate may be advantageously reacted with about 75 mole percent to about 125 mole percent of concentrated sulfuric acid. The upper limit of the sulfuric acid reactant is determined by the fact that large excesses of sulfuric acid will significantly reduce the yield of pyruvic acid by the reaction of the excess acid with the pyruvic acid product. This limit may readily be determined by those skilled in the art. Preferably, approximately equal molar quantities of the sulfuric acid and the potassium bitartrate are reacted. However, acceptable results are obtained when the potassium bitartrate is reacted with slightly less sulfuric acid, e.g., 95 to 98 mole percent.

The reaction is preferably carried out at a temperature of from about 160° C. to about 270° C. Although some pyruvic acid will be formed at temperatures below 160° C., since the boiling point of pyruvic acid is about 165° C., at temperatures below 160° C. the product cannnot be removed from the reaction vessel by distillation. At temperatures greater than about 270° C., pyruvic acid begins to decompose, thereby significantly reducing the yield of pyruvic acid product.

In one preferred embodiment, the present invention comprises charging a suitably sized reaction vessel with a quantity of potassium bitartrate and approximately 95 to 98 mole percent of concentrated sulfuric acid. The mixture is then heated with a heating mantel. The temperature within the reaction vessel quickly increases to about 120° C. to 130° C. The temperature will then increase relatively slowly to about 210° C. The pyruvic acid is preferably removed from the reaction vessel by distillation and at about 165° C. the pyruvic acid will begin to distill out from the reaction vessel. The distillation will continue until the reaction goes to completion. The mixture is heated for a period of from about one half hour to about one hour. Upon reaching about 210° C., the temperature inside the reaction vessel will again begin to increase relatively rapidly.

It should be noted that during the reaction a significant amount of foam is formed in the reaction vessel. The foam moves up the distillation column and thereby prevents removal of the pyruvic acid from the reaction vessel by distillation. It is, therefore, necessary to utilize a foam control device to enable the distillation of the pyruvic acid from the reaction vessel. A particularly effective foam control device comprises a paddle which is rotated over the surface of the liquid during the course of the reaction. The paddle functions to disperse the foam by pushing it against the side of the reaction vessel. An ultrasonic foam dispersion device can also be employed in the practice of the present invention. Alternatively, the reaction can be carried out in a large oversized vessel wherein the foam will disperse prior to entering the distillation column. It will be obvious to one skilled in the art that other suitable methods of foam control can also be employed in the practice of the present invention.

The crude pyruvic acid which is recovered by distillation may then be refined by vacuum distillation to form a high purity pyruvic acid. The high purity product is preferably collected between 54° C. to 58° C. at approximately 10mm Hg.

The following examples illustrate the invention. However, it is to be understood that these examples are given primarily by way of illustration and not of limitation.

EXAMPLE 1

Sulfuric acid (69.4 grams of 66° Be') was added to a 1-liter round bottom, 3-neck flask which was fitted with a stirrer and a thermometer. While the acid was being stirred, an approximately equal molar amount (130.6 grams) of potassium bitartrate was added to the flask to form a thick paste. The mixture was then heated with a heating mantel to a temperature of approximately 240° C. The foam produced during the reaction was controlled using the device comprising a rotating paddle as disclosed heretofore in the specification. After approximately 40 minutes, a total of 66 grams of distillate had been collected, representing the yield of approximately 90%. Upon refining, the crude distillate provided 52 grams of high purity pyruvic acid, representing approximately an 85% yield.

EXAMPLE 2

The reaction was the same as that described in Example 1 except that the mixture was heated for a period of 50 minutes to a temperature of 264° C. The amount of crude distillate collected represented approximately a 95% yield.

EXAMPLE 3

Sulfuric acid (347 grams of 66° Be') was added to a 5-liter flask which was fitted with a thermometer and a stirrer. With stirring, an equal molar amount of potassium bitartrate (653 grams) was added to the flask to form a thick paste. The mixture was then heated with a heating mantel. After approximately 30 minutes, the internal temperature had reached approximately 170° C. and distillation had commenced. The foam produced during the reaction was controlled using the device and method disclosed heretofore in the application. After 65 minutes, the internal temperature was approximately 260° C. and the reaction was complete. The crude distillate amounted to approximately an 89% yield.

While an embodiment and application of this invention has been shown and described, it will be apparent to those skilled in the art that many more modifications are possible without departing from the inventive concepts herein described. The invention, therefore, is not to be restricted except as is necessary by the prior art and by the spirit of the appended claims.

What is claimed is:

1. A process for the production of pyruvic acid comprising reacting concentrated sulfuric acid with a salt of bitartrate at a temperature from about 160° C. to about 270° C.

2. The process of claim 1 wherein said salt is the potassium salt of bitartrate.

3. The process of claim 2 wherein said potassium bitartrate is reacted with from about 75 mole percent to about 125 mole percent of said sulfuric acid.

4. The process of claim 2 wherein said potassium bitartrate is reacted with approximately 95 to 98 mole percent of said sulfuric acid.

5. The process of claim 2 wherein said process comprises the additional step of vacuum distilling said pyruvic acid at a temperature of between 54° C. and 58° C. at approximately 10 mm of mercury.

6. A process for the production of pyruvic acid comprising reacting approximately equal molar quantities of concentrated sulfuric acid and potassium bitartrate at a temperature of from about 160° C. to about 270° C.

7. The process of claim 1 wherein said salt is the sodium salt of bitartrate.

8. A process for the production of pyruvic acid comprising reacting approximately equal molar quantities of concentrated sulfuric acid and sodium bitartrate at a temperature from about 160° C. to about 270° C.

* * * * *